United States Patent [19]
Dow et al.

[11] Patent Number: 5,326,905
[45] Date of Patent: Jul. 5, 1994

[54] BENZYLPHOSPHONIC ACID TYROSINE KINASE INHIBITORS

[75] Inventors: Robert L. Dow, Waterford; Steven W. Goldstein, Mystic, both of Conn.

[73] Assignee: Pfizer Inc., New York, N.Y.

[21] Appl. No.: 934,469

[22] PCT Filed: Mar. 14, 1991

[86] PCT No.: PCT/US91/01731
§ 371 Date: Sep. 16, 1992
§ 102(e) Date: Sep. 16, 1992

[87] PCT Pub. No.: WO91/15495
PCT Pub. Date: Oct. 17, 1991

[51] Int. Cl.$^5$ .............................................. C07F 9/44
[52] U.S. Cl. .......................................... 562/8; 562/15
[58] Field of Search ................................. 562/8, 15

[56] References Cited
PUBLICATIONS

Okamoto, et al. Phosphorus Sulfur 35(1-2) 77-81 1988.
Okamoto, Y., et al., "Photochemical C-P Bond Cleavage of Some (Substituted Benzyl) phosphonic Acid Derivatives," J. Chem. Soc. Japan, No. 7:1255-1261 (1987).
Okamoto, Y., et al., "Photochemical C-P Bond Cleavage of Benzoylbenzylphosphonic Acids," Phosphourus and Sulfur, v. 35:77-81 (1988).
Petrakis, K. S., et al., "Palladium-Catalyzed Substitutions of Triflates Derived from Tyrosine-Containing Peptides and Simpler Hydroxyarenes Forming 4-(Diethoxyphosphinyl)phenylalanines and Diethyl Arylphosphonates," J. Am. Chem. Soc., 109:2831-2833 (1987).
Saperstein, R., et al., "Design of a Selective Insulin Receptor Tyrosine Kinase Inhibitor and Its Effect on Glucose Uptake and Metabolism in Intact Cells," Biocheminstry, 28:5694-5701 (1989).

*Primary Examiner*—Joeé G. Dees
*Assistant Examiner*—Joseph M. Conrad, III
*Attorney, Agent, or Firm*—Peter C. Richardson; Gregg C. Benson; A. Dean Olson

[57] ABSTRACT

Certain benzylphosphonic acid compounds, and their pharmaceutically-acceptable salts, are inhibitors of tyrosine kinase enzymes, and so are useful for the control of tyrosine kinase dependent diseases (e.g., cancer, atherosclerosis).

7 Claims, No Drawings

BENZYLPHOSPHONIC ACID TYROSINE KINASE INHIBITORS

TECHNICAL FIELD

This invention relates to acid compounds which are useful in the field of medicinal chemistry. More particularly the invention relates to benzylphosphonic acid compounds which are tyrosine kinase inhibitors useful for the control of cancer, antiangiogenesis and atherosclerosis.

BACKGROUND OF THE INVENTION

Tyrosine-specific protein kinases (tyrosine kinases) represent a family of enzymes which catalyze the transfer of the terminal phosphate of adenosine triphosphate to tyrosine residues in protein substrates. The first members of this class to be identified were tyrosine kinases associated with viral genes (termed oncogenes) which were capable of cell transformation (i.e. pp60v-src and pp98v-fps). Later it was shown that there were normal cellular counterparts (i.e. pp60c-src and pp98c-fps) to these viral gene products. A third category of tyrosine kinases to be identified are those termed the growth factor receptors, which includes insulin, epidermal growth factor, and p185HER-2 receptors. All of these tyrosine kinases are believed, by way of substrate phosphorylation, to play critical roles in signal transduction for a number of cell functions.

Though the exact mechanisms of signal transduction have yet to be elucidated, tyrosine kinases have been shown to be important contributing factors in cell proliferation, carcinogenesis and cell differentiation. Therefore, inhibitors of these tyrosine kinases are useful for the prevention and chemotherapy of proliferative diseases dependent on these enzymes.

SUMMARY OF THE INVENTION

This invention is directed to benzylphosphonic compounds that are useful as tyrosine kinase inhibitors. The compounds of this invention have the formula

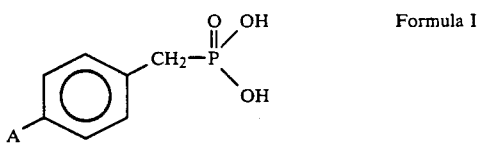

Formula I and the pharmaceutically-acceptable cationic salts thereof, in which A can be a wide variety of lipophilic groups which are neither strongly basic nor strongly acidic. Typical groups for A are -phenyl, -benzoyl,

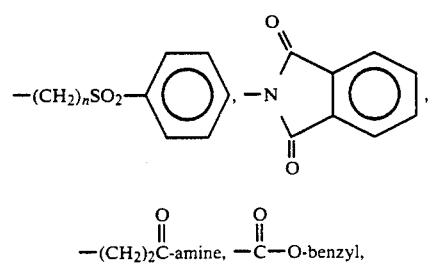

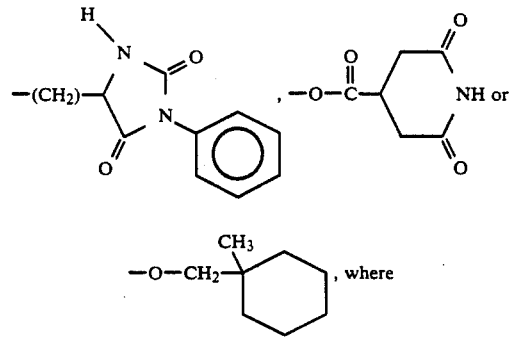

$n = 0$ or 1. "Amine" represents the radical NH-R, where $NH_2$—R is an esterified derivative of a naturally-occurring amino acid. Representative groups of NH-R are

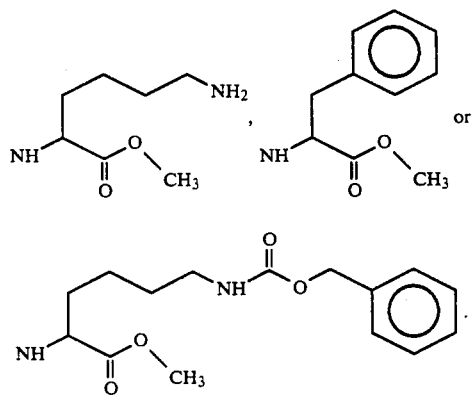

The present invention is also directed to pharmaceutical compositions for the control of tyrosine kinase dependent diseases in mammals which comprise a compound of the formula (I) in a pharmaceutically-acceptable carrier; and to a method of controlling tyrosine kinase dependent diseases which comprises administering to a mammal suffering from tyrosine kinase dependent diseases a tyrosine kinase dependent disease controlling amount of a compound of the formula (I).

The expression "pharmaceutically-acceptable cationic salt" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

Other features and advantages will be apparent from the specification and claims.

DETAILED DESCRIPTION OF THE INVENTION

In general, the phosphonic acid compounds of this invention of formula I can be prepared by reacting the appropriate benzyl halide of formula II with a phosphite (the Arbusov reaction), followed by hydrolysis, as follows

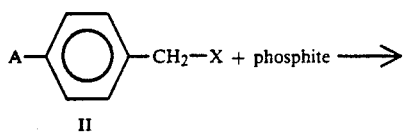

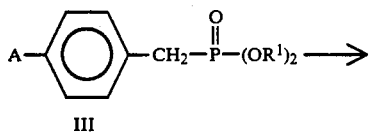

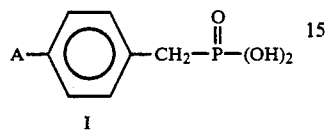

These reactions are carried out by standard methods, well-known in the art.

Reaction of the benzyl halide of formula II with the phosphite is usually carried out by heating with a phosphite at temperatures of about ambient (25° C.) to about 150° C., preferably about 60° C. to about 90° C., for about one to about 24 hours. Typically an excess of phosphite (e.g., 1.2 equivalents to about 10 equivalents) is used. The reaction may be run neat (typically with at least about a 5 equivalent excess of phosphite) or may be run in nonhydroxylic solvents such as nonpolar hydrocarbon solvents, ethereal solvents, etc. Specific examples include THF, DMF and toluene. Typically the reaction is run at ambient pressure although any pressure that does not adversely affect the desired end product may be used. A number of phosphite compounds can be used. However, particularly suitable are phosphite esters such as triethyl phosphite or tristrimethylsilylphosphite.

The manner of carrying out the hydrolysis step depends to some extent on the nature of the ester (i.e., the nature of the group $R^1$). For example, when a triethyl phosphite is used (i.e., $R^1$ is ethyl), the benzyl phosphonic ester is heated (e.g., refluxed) with a concentrated mineral acid such as hydrochloric acid for about 12 to about 36 hours. Typically the hydrolysis is performed in the absence of a solvent (except for the acid). The reaction is conveniently performed at ambient pressure although any pressure that does not deleteriously affect the desired end product may be used.

When a trialkylsilyl ester is used, milder hydrolysis conditions such as stirring at about 0° C. to about 50° C. for about 2 to about 12 hours in a water miscible solvent such as THF, acetone or alcohols are sufficient. Water, typically about 5% to about 30% by volume of solvent, is used to effect the hydrolysis. Although any pressure that does not deleteriously affect the desired end product may be used, the reaction is conveniently carried out at ambient pressure. The intermediate phosphonate ester of formula II can be isolated and purified, if desired. Alternatively, the intermediate ester can be hydrolysed in situ.

The phosphonic acids of formula I can be isolated and purified by standard methods. For example, standard recrystallization or chromatograph procedures may be used; however, recrystallization is preferred.

The starting halides of formula II can be made by a number of methods. The method will tend to vary somewhat, depending on the particular value of the A group, but an appropriate method will be selected readily by one skilled in the art. For example, some of the benzyl halides of the formula II of this invention may be made by benzylic bromination, as described empirically below, of the appropriate toluene-based starting compound (IV) appropriately substituted to achieve the desired A functionality.

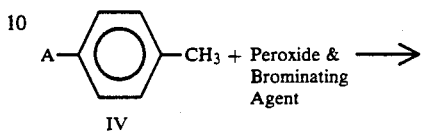

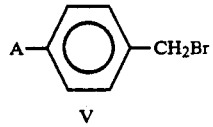

Preferably the benzyl compound (IV) is reacted with a brominating agent such as N-bromosuccinimide in the presence of a peroxide such as benzoyl peroxide in a aprotic solvent such as carbon tetrachloride at reflux to produce the benzyl bromide (V).

Some of the starting compounds for the benzylic bromination may be made by making the acid chloride of the appropriate acid (e.g., dihydrocitrazinic acid), preferably by refluxing with thionyl chloride. The acid chloride is esterified by reaction with the paramethylphenol to yield the desired toluene-based starting compounds.

Other starting compounds for the benzylic bromination may be made by basic treatment of paramethylphenol. Preferably, the paramethylphenol is reacted with potassium hydroxide in alcohol at room temperature, to yield the phenoxide followed by reaction with the appropriate methyl tosylate and potassium iodide at about 150° C. to yield the desired toluene based starting compound.

For compounds that can't employ a benzylic halogenation an alternative synthetic route, as depicted empirically below, is to condense an acid chloride (VI) (having a benzyl halide in the para position) with an appropriate amine or alcohol to yield an amide or ester (VII).

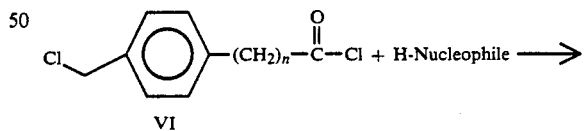

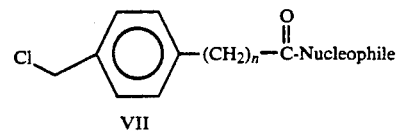

n=1, 2 or 3, H-Nucleophile=amine or alcohol.

Preferably, the acyl halide is reacted with an amine or alcohol under nitrogen at about 0° C. to about 25° C. in the presence of a base such as triethylamine and an aprotic solvent such as methylene chloride. The resulting amide or ester can then be condensed with a phosphite as described above.

The starting benzyl chlorides used in the above reaction sequence may be formed by bromomethylation and conversion to the acylchloride (X) as described empirically below, of the appropriate acid (VIII).

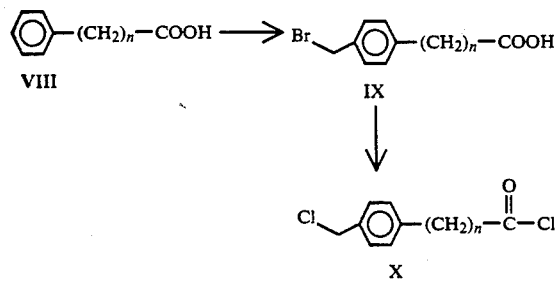

Preferably 3-phenylpropionic acid is heated with paraformaldehyde and HBr at about 25° C. to about 100° C. Preferably the acid (IX) is reacted with oxalylchloride under nitrogen at ambient temperature.

Yet other benzyl phosphonic acid based compounds can be prepared by condensing the appropriate hydantoin (XI) with bis-benzyl halides (XII) as described empirically below.

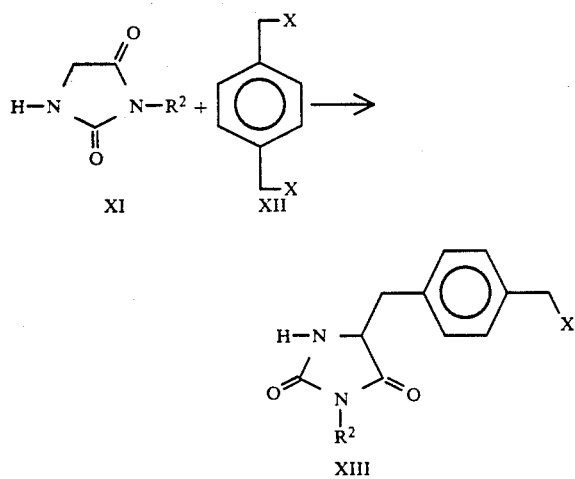

wherein $R^2$ is a lipophilic constituent such as phenyl and X is halogen (i.e., chlorine, bromine, iodine or fluorine). Preferably an N-3 protected hydantoin is treated with a base such as magnesium methoxycarbonate at temperatures from about 25° C. to about 120° C. in an aprotic solvent followed by treatment with a dihalide at a similar temperature.

The hydantoin starting compounds (XI) may be made by reaction of an amine with ethyl isocyanatoacetate followed by treatment with acid.

The starting materials for the above described three major reaction pathways, benzylic halogenation, condensation of acid chloride with amine or alcohol and condensation of bis-benzyl halides with hydantoins, can be easily synthesized by those skilled in the art starting from common chemical reagents using conventional methods of organic synthesis.

The compounds of this invention are acidic and they form base salts. All such base salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

The compounds of this invention are all readily adapted to therapeutic use as tyrosine kinase inhibitors for the control of tyrosine kinase dependent diseases in mammals. Tyrosine kinase dependent diseases refer to hyperproliferative disorders which are initiated/maintained by aberrant tyrosine kinase enzyme activity. Examples include cancer, atherosclerosis, antiangiogenersis (e.g., tumor growth, diabetic retinopathy), etc.

The compounds are administered either orally or parenterally, or topically as eye drops, in dosages ranging from about 0.1 to 10 mg/kg of body weight per day in single or divided doses. Of course, in particular situations, at the discretion of the attending physician, doses outside of this range will be used.

The compounds of this invention can be administered in a wide variety of different dosage forms, i.e., they may be combined with various pharmaceutically-acceptable inert carriers in the form of tablets, capsules, lozenges, troches, hard candies, powders, sprays, elixirs, syrups, injectable or eye drop solutions, and the like. Such carriers include solid diluents or fillers, sterile aqueous media and various non-toxic organic solvents. For purposes of oral administration, tablets containing various excipients such as sodium citrate, calcium carbonate and calcium phosphate are employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the essential active ingredient therein can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble, alkali metal or alkaline-earth metal salts previously enumerated. Such aqueous solutions should be suitable buffered, if necessary, and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of topical administration, dilute sterile, aqueous solutions (usually in about 0.1% to 5% concentration), otherwise similar to the above parenteral solutions, are prepared in containers suitable for dropwise administration to the eye.

In a pharmaceutical composition comprising a compound of formula I, or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

It should be understood that the invention is not limited to the particular embodiments shown and described herein, but that various changes and modifications may be made without departing from the spirit and scope of this novel concept as defined by the following claims.

EXAMPLE 1

1. 4-benzoylbenzyl bromide

To a solution of 4.0 g (20 mmol) of 4-benzoyltoluene and 3.6 g (20 mmol) of N-bromosuccinimide in 120 ml of carbon tetrachloride was added 0.05 g (0.2 mmol) of benzoyl peroxide. The reaction was refluxed for 17 hours, cooled to room temperature and filtered. The filtrate was evaporated and the crude product was taken on without further purification.

2. 4-benzoylbenzylphosphonic acid

A mixture of 4.8 g of 4-benzoylbenzyl bromide and triethylphosphite was heated at 125° C. for 0.5 hours and cooled to room temperature. The resulting oil was purified by flash chromatography (70% ethyl acetate/hexanes) to afford 3.2 g of diethyl 4-benzoylbenzylphosphonic acid, as an oil. A mixture of 3.2 g (9.6 mmol) of diethyl 4-benzoylbenzylphosphonic acid and 40 ml of concentrated hydrochloric acid was refluxed for 7 hours and cooled to room temperature. The two phase mixture was partitioned between 125 ml of water and 400 ml of EtOAc, the EtOAc layer was dried over $Na_2SO_4$, filtered and evaporated to give 0.7 g of product; m.p. 172°–175° C.

Analysis calculated for $C_{14}H_{13}O_4P$: C, 60.87; H, 4.74%. Found: C, 60.94; H, 4.66%.

EXAMPLE 2

1. 4-(Phenylsulfonyl)benzyl bromide was prepared from 4-(phenylsulfonyl)toluene according to Example 1, part 1.

2. 4-(phenylsulfonyl)benzylphosphonic acid

A solution of 4.3 g (14 mmol) of 4-(phenylsulfonyl)benzyl bromide and 30 g (0.1 mole) of tris-trimethylsilylphosphite was heated at 120° C. for 18 hours. The excess tris-trimethylsilylphosphite was distilled off under reduced pressure. The residue was dissolved in 200 ml of 9:1 tetrahydrofuran/water and was allowed to stand at room temperature for 18 hours. The tetrahydrofuran was evaporated and the resulting solids were filtered and washed with water to give 1.4 g of product; m.p. 217–219° C.

Analysis calculated for $C_{13}H_{13}O_5PS$: C, 50.00; H, 4.20%. Found: C, 50.00; H, 4.14%.

EXAMPLE 3

1. N-[4(bromomethyl)phenyl]phthalimide

The title compound was prepared from N-[4(methyl)phenyl]phthalimide according to the procedure of Example 1, part 1.

2. 4-(N-phthalimidyl)benzylphosphonic acid

The title compound was prepared from N-[4(bromomethyl)phenyl]phthalimide according to the procedure of Example 2, part 2; m.p. 239°–243° C.

Analysis calculated for $C_{15}H_{12}NO_5P$: C, 56.79; H, 3.81; N, 4.42%. Found: C, 57.04; H, 3.74; N, 4.45%.

EXAMPLE 4

1. 4-[((1-methyl)cyclohexyl)methoxy]toluene

To a cooled (0° C.), stirred solution of 8.4 g (0.15 mole) of potassium hydroxide in 100 ml of MeOH was added 13.5 g (0.12 mole) of 4-methylphenol over a 15 minute period. The reaction was stirred at room temperature for 0.5 hour and MeOH was evaporated to afford a solid. A solution of this solid, 28.2 g (0.1 mole) of ((1-methyl)cyclohexyl)methyl tosylate and 1.4 g of potassium iodide were heated at 150° C. for 5 hours. The reaction was cooled to room temperature, poured onto ice-water and extracted with EtOAc. The EtOAc layer was washed with 2N aqueous NaOH, brine, dried over $MgSO_4$, filtered and evaporated. The resulting oil was filtered through a plug of silica gel to give 20 g of product as an oil.

2. 4-[((1-methyl)cyclohexyl)methoxy]benzyl bromide

A solution of 2.2 g (10 mmol) of 4-[((1-methyl)cyclohexyl)methoxy]toluene, 1.8 g (10 mmol) of N-bromosuccinimide and 0.02 g of benzoyl peroxide in 60 ml of carbon tetrachloride was refluxed for 16 hours. The reaction was cooled to room temperature, filtered and the filtrate evaporated to give the product which was used without further purification.

3. diethyl 4-[((1-methyl)cyclohexyl)methoxy]benzylphosphonate

A mixture of the 4-[((1-methyl)cyclohexyl)methoxy]benzyl bromide and 1.7 g (10 mmol) of triethylphosphite was heated at 145° C. for 0.2 hour. The reaction was cooled to room temperature and flash chromatographed to give 1.3 g of product as an oil.

4. 4-[((1-methyl)cyclohexyl)methoxy]benzylphosphonic acid

A solution 0.7 g (2.0 mmol) of diethyl 4-[((1methyl)cyclohexyl)methoxy]benzylphosphonate and 10 ml of concentrated hydrochloric acid was refluxed for 24 hours. The reaction was cooled to room temperature, filtered and the solids were washed with water. The solids were recrystallized from EtOAc/cyclohexane to give 0.4 g of the product; m.p. 170°–172° C.

Analysis calculated for $C_{15}H_{23}O_4P$: C, 60.39; H, 7.77%. Found: C, 60.73; H, 7.87%.

EXAMPLE 5

1. 4-(4-methylphenoxy)carboxyglutarimide

A solution of 46 g (0.3 mole) of dihydrocitrazinic acid in 350 ml of thionyl chloride was refluxed for 6 hours, cooled to room temperature and evaporated to dryness. The resulting solids were recrystallized from benzene to give 33 g of dihydrocitrazinoyl chloride; m.p. 120°–121.5° C. A solution of 6.0 g (34 mmol) of dihydrocitrazinoyl chloride, 3.7 g (34 mmol) of 4-methylphenol and 3 ml of pyridine in 60 ml of p-dioxane was refluxed for 2 hours. The upper layer was separated, cooled to room temperature and the solids were isolated by filtration. The solids were recrystallized from acetone to give 1.2 g of product; m.p. 183°–184° C.

Analysis calculated for $C_{13}H_{13}NO_4$: C, 63.15; H, 5.66; N, 5.26%. Found: C, 63.22; H, 5.74; N, 5.47%.

2. 4-[4-(bromomethyl)phenoxy]carboxyglutarimide

A solution of 1.3 g (5.2 mmol) of 4-(4-methylphenoxy)carboxyglutarimide, 1.0 g (5.7 mmol) of N-bromosuccinimide and 0.02 g of benzoyl peroxide in 30 ml of carbon tetrachloride was refluxed for 16 hours, cooled to room temperature, evaporated and the residue dissolved in 200 ml of ethyl acetate. The EtOAc layer was washed with water, dried over $Na_2SO_4$ and evaporated to give 1.6 g of the crude product.

3. 4-[(4-methylphosphonic acid)phenoxy]carboxyglutarimide

The titled compound was prepared from 4-[4-(bromomethyl)phenoxy]carboxyglutarimide according to Example 2, part 2; m.p. 242°–244° C.

Analysis calculated for $C_{13}H_{14}NO_7P$: C, 47.71; H, 4.31; N, 4.28%. Found: C, 47.53; H, 4.22; N, 4.30%.

EXAMPLE 6

1. benzyl 4-(chloromethyl)benzoic acid

A stirred suspension of 3.0 g (14 mmol) of 4-(bromomethyl)benzoic acid and 3.5 ml (41 mmol) of oxalyl chloride in 35 ml of dichloromethane was refluxed for 10 hours and cooled to room temperature. Evaporation afforded 4-(chloromethyl)benzoyl chloride as an oil which was used without purification. To a cooled (0° C.) solution of 2.6 g (14 mmol) of 4-(chloromethyl)benzoyl chloride and 2.0 g (18 mmol) of benzyl alcohol in 30 ml of dichloromethane was added 1.8 g (18 mmol) of triethylamine. The reaction was stirred at 0° C. for 0.2 hours, then at room temperature for an additional 1 hour and poured into 150 ml of EtOAc. The EtOAc layer was with three portions of water, dried over $Na_2SO_4$, filtered and evaporated. The crude product was flash chromatographed (5% EtOAc/hexanes) to give 0.7 g of product; m.p. 52°–54° C.

2. benzyl 4-(methylphosphonic acid)benzoic acid

The titled compound was prepared from benzyl 4-(chloromethyl)benzoic acid according to the procedure of Example 2, part 2; m.p. 160°–163° C.

EXAMPLE 7

1. 3-[4-(chloromethyl)phenyl]propionyl chloride

A solution of 1.5 g (6.2 mmol) of 3-[4-(bromomethyl)phenyl]propionic acid (U.S. Pat. No. 4,032,533) and 1.2 g (9.3 mmol) of oxalyl chloride in 6 ml of dichloromethane was stirred at room temperature for 2.5 hours and evaporated to give 1.6 g of product as an oil.

2. N-[3-(4-(chloromethyl)phenyl)propionyl]phenylalanine, methyl ester

To a cooled (0° C.), stirred solution of 1.6 g (6.2 mmol) of 3-[4-(chloromethyl)phenyl]propionyl chloride and 1.3 g (6.2 mmol) of phenylalanine methyl ester hydrochloride salt in 6 ml of dichloromethane was added 1.4 g (14 mmol) of triethylamine. The reaction mixture was stirred at 0° C. for 0.5 hour, poured into EtOAc and washed with water. The EtOAc layer was dried over $Na_2SO_4$, filtered and evaporated to afford an oil. This oil was flash chromatographed (40% EtOAc/hexanes) to give 0.8 g of product; m.p. 89°–90° C.

Analysis calculated for $C_{20}H_{22}ClNO_3$: C, 66.66; H, 6.15; N, 3.88%. Found: C, 66.85; H, 6.19; N, 3.69%.

3. N-[3-(4-(methylphosphonic acid)phenyl)propionyl]phenylalanine methyl ester The titled compound was prepared from N-[3-(4-(chloromethyl)phenyl)propionyl]phenylalanine methyl ester according to the procedure of Example 2, part 2; m.p. 139°–142° C.

Analysis calculated for $C_{20}H_{24}NO_6P$: C, 59.26; H, 5.97; N, 3.46%. Found: C, 58.97; H, 5.85; N, 3.43%.

EXAMPLE 8

1. N-ε-carboxybenzyloxy-N-[3-(4-(chloromethyl)phenyl)-propionyl]lysine, methyl ester To a cooled, (0° C.), stirred slurry of 1.6 g (6.2 mmol) of 3-[4-(chloromethyl)phenyl]propionyl chloride and 2.0 g (6.2 mmol) of N-ε-carboxybenzyloxylysine methyl ester hydrochloride salt in 6 ml of dichloromethane was added 1.4 g (14 mmol) of triethylamine. The reaction was stirred at room temperature for 2 hours, poured into EtOAc and washed with water. The EtOAc layer was dried over $Na_2SO_4$, filtered and evaporated to afford an oil. This oil was flash chromatographed (55% EtOAc/hexanes) to give 2.1 g of product; m.p. 98°–101° C.

Analysis calculated for $C_{25}H_{31}ClN_2O_5$: C, 63.21; H, 6.58; N, 5.90%. Found: C, 63.47; H, 6.59; N, 6.02%.

2. N-ε-carboxybenzyloxy-N-[3-(4-methylphosphonic acid)phenyl)propionyl]lysine, methyl ester The titled compound was made from the above product using the procedure in Example 2, part 2; m.p. 83° C.

Analysis calculated for $C_{25}H_{33}N_2O_8P \cdot \frac{1}{2}H_2O$: C, 56.71; H, 6.47; N, 5.29%. Found: C, 56.56; H, 6.21; N, 5.36%.

3. N-[3-(4-(methylphosphonic acid)phenyl)propionyl]lysine, methyl ester

A slurry of 0.63 g (1.2 mmol) of N-ε-carboxybenzyloxy-N-[3-(4-(methylphosphonic acid)phenyl)propionyl]lysine, methyl ester and 0.5 g of 10% palladium on carbon in 17 ml of MeOH was subjected to 30 psi hydrogen for 4.5 hours. Evaporation of MeOH afforded a mass which was continuously extracted with hot MeOH for 72 hours. Evaporation afforded a solid which was dissolved in 40 ml of hot water, filtered and the filtrate was evaporated to give 136 mg of product; m.p. 262°–264° C.

Analysis calculated for $C_{17}H_{27}N_2O_6P \cdot \frac{1}{3}H_2O$: C, 52.04; H, 7.11; N, 7.14%. Found: C, 52.11; H, 6.93; N, 6.99%.

EXAMPLE 9

1. ethyl δ-phenyl hydantoate

To a cooled (0° C.), stirred solution of 6.5 g (50 mmol) of ethyl isocyanatoacetate in 75 ml of ethyl ether was added a solution of 4.7 g (50 mmol) of aniline in 50 ml of ethyl ether. The reaction was warmed to room temperature, stirred for 0.5 hour, evaporated to two-thirds the original volume, cooled to 0° C. and filtered to give 8.2 g of product; m.p. 110°–111° C.

2. 3-phenylhydantoin

A solution of 5.6 g (25 mmol) of ethyl δ-phenyl hydantoate in 25 ml of 6N hydrochloric acid was heated at 100° C. for 1 hour and then cooled to 0° C., Filtration gave 3.6 g of product; m.p, 154°–156° C.

3. 4-(4-chloromethylbenzyl)-3-phenyhydantoin

To 8.8 ml of a 2M solution of magnesium methyl carbonate in dimethylformamide was added 0.9 g (5.0 mmol) of 3-phenylhydantoin and the resulting mixture was heated at 90° C. for 0.5 hour. To the reaction was added 8.8 g (50 mmol) of 4-(chloromethyl)benzyl chloride and the reaction was maintained at 90° C. for 0.5 hour. The reaction was poured onto 75 g of ice, 15 ml of 1N hydrochloric acid added and the resulting mixture stirred for 0.2 hour. The reaction was extracted with 250 ml of EtOAc, the organic layer was washed with water, dried over $Na_2SO_4$, filtered and evaporated to give a solid. This solid was flash chromatographed (60% EtOAc/hexanes) to give 1.2 g of product; m.p. 167°–168° C.

Analysis calculated for $C_{17}H_{15}ClN_2O_2$: C, 64.86; H, 4.80; N, 8.90%. Found: C, 64.76; H, 4.78; N, 8.75%.

4. 4-[(4-methylphosphonic acid)benzyl]-3-phenylhydantoin

The titled compound was made from the above product using the procedure of Example 2, part 2; m.p. 190°–192° C.

Analysis calculated for $C_{17}H_{17}N_2O_5P$: C, 56.34; H, 4.76; N, 7.78%. Found: C, 56.34; H, 4.66; N, 7.76%.

EXAMPLE 10

1. diethyl 4-phenylbenzylphosphonate

A stirred mixture of 5.0 g (20 mmol) of commercially available 4-bromomethyldiphenyl and 4.4 g ( 26 mmol) of triethylphosphite was heated at 120° C. for 3 hours and then allowed to cool to room temperature. The resulting oil was purified by flash chromatography (500 g 60% EtOAc/hexanes) to give 5.4 g of product; m.p. 55°–58° C.

Analysis calculated for $C_{17}H_{21}O_3P$: C, 67.09; H, 6.96%. Found: C, 66.85; H, 6.97%.

2. 4-phenylbenzylphosphonic acid

A vigorously stirred suspension of 3.5 g (12 mmol) of diethyl 4-phenylbenzylphosphonate in 35 ml of concentrated hydrochloric acid was refluxed for 45 hours and cooled to room temperature. The solids were filtered, washed with water and then recrystallized from EtOH to give 0.5 g of product; m.p. 246°–248° C.

Analysis calculated for $C_{13}H_{13}O_3P$: C, 62.90; H, 5.28%. Found: C, 62.86; H, 5.22%.

EXAMPLE 11

4-(phenylsulfonylmethyl)benzylphosphonic acid

Commercially available 4-(phenylsulfonylmethyl)-benzyl bromide was converted according to the procedure of Example 2, part 2 to 4-(phenylsulfonylmethyl)-benzylphosphonic acid; m.p. >280° C.

Analysis calculated for $C_{14}H_{15}O_5PS$: C, 51.53; H, 4.63%. Found: C, 51.65; H, 4.61%.

We claim:

1. A compound of the formula

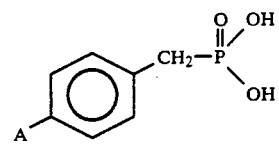

Formula I wherein A is,

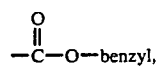

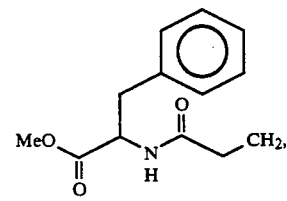

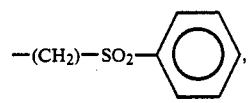

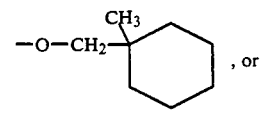

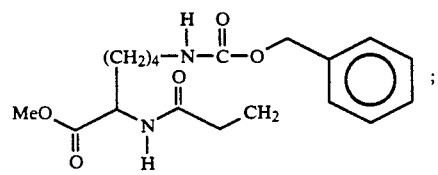

and the pharmaceutically-acceptable cationic salts thereof.

2. A compound of claim 1, wherein A is

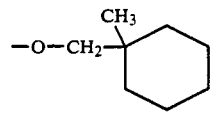

3. A compound of claim 1, wherein A is

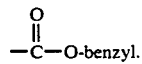

4. A compound of claim 1, wherein A is

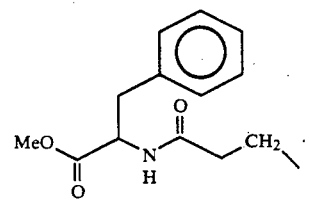

5. A compound of claim 1, wherein A is

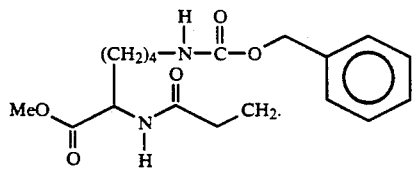

6. A pharmaceutical composition for the control of tyrosine kinase dependent diseases in mammals which comprises a compound of claim 1 in a pharmaceutically-acceptable carrier.

7. A method of controlling tyrosine kinase dependent diseases which comprises administering to a mammal suffering from tyrosine kinase dependent diseases a tyrosine kinase dependent disease controlling amount of a compound of claim 1.

* * * * *